United States Patent [19]

Hovey

[11] 4,176,666

[45] Dec. 4, 1979

[54] GAS SCAVENGER SYSTEM

[76] Inventor: Thomas C. Hovey, 23 Mt. Desert Dr., Bangor, Me. 04401

[21] Appl. No.: 838,568

[22] Filed: Oct. 3, 1977

Related U.S. Application Data

[63] Continuation-in-part of Ser. No. 691,357, Jun. 1, 1976, abandoned.

[51] Int. Cl.² .............................................. A61M 17/00
[52] U.S. Cl. ............................... 128/205.24; 128/276; 137/526; 137/DIG. 4
[58] Field of Search .......... 128/188, 202, 145.5-145.8, 128/276, 277, 142.3, 146.5; 137/DIG. 4, 217, 526, DIG. 8, 859, 852, 542, 512.15; 251/331

[56] References Cited

U.S. PATENT DOCUMENTS

| | | | |
|---|---|---|---|
| 2,427,419 | 9/1947 | Rausch | 137/526 X |
| 2,546,678 | 3/1951 | Rockwell | 137/526 X |
| 3,088,456 | 5/1963 | Stanton | 128/202 X |
| 3,095,905 | 7/1963 | Glauber | 251/331 |
| 3,145,724 | 8/1964 | Pelzer | 137/526 X |
| 3,419,009 | 12/1968 | Ericson | 137/217 X |
| 3,548,822 | 12/1970 | Seeler et al. | 128/145.5 X |
| 3,566,867 | 3/1971 | Dryden | 128/188 |
| 3,721,239 | 3/1973 | Myers | 128/188 |
| 3,800,793 | 4/1974 | Marrese et al. | 128/188 X |
| 3,830,241 | 8/1974 | Dye et al. | 137/526 X |

FOREIGN PATENT DOCUMENTS

| | | | |
|---|---|---|---|
| 520774 | 7/1953 | Belgium | 137/DIG. 4 |
| 2213764 | 9/1973 | Fed. Rep. of Germany | 128/188 |

*Primary Examiner*—Henry J. Recla
*Attorney, Agent, or Firm*—Robert D. Farkas

[57] ABSTRACT

This disclosure pertains to a gas scavenger apparatus utilized to recover anesthesia-logical gases derived during surgical procedures and to dispose same to a closed vacuum line substantially limiting the inadvertant escapage into the atmosphere. A reservoir bag is connected to the patient's anesthetic circuit, which in turn is connected to a scavenger valve. The vacuum line constantly empties the reservoir bag drawing off the waste gas accumulated therein. When the reservoir bag is substantially empty, a valve admits ambient air, as well as waste gas, into a chamber emptied by the vacuum line. Thus, the vacuum line does not act on the patient's anesthetic circuit, serving only to empty the reservoir bag as waste gas accumulates therein.

7 Claims, 9 Drawing Figures

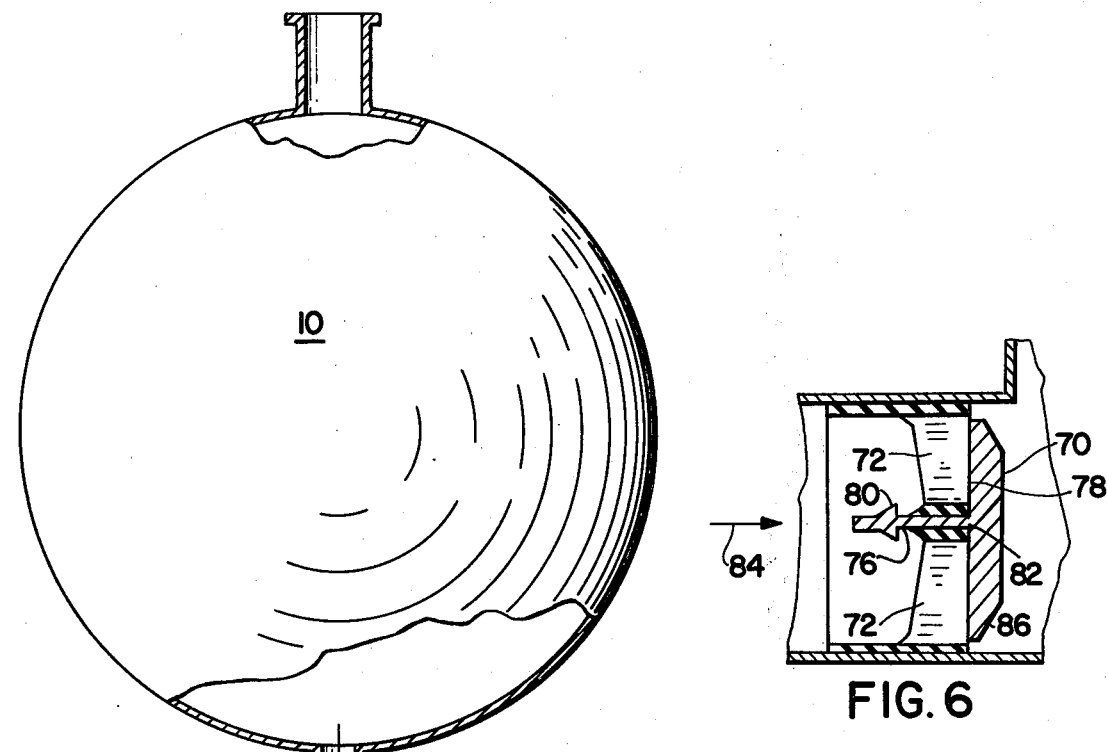
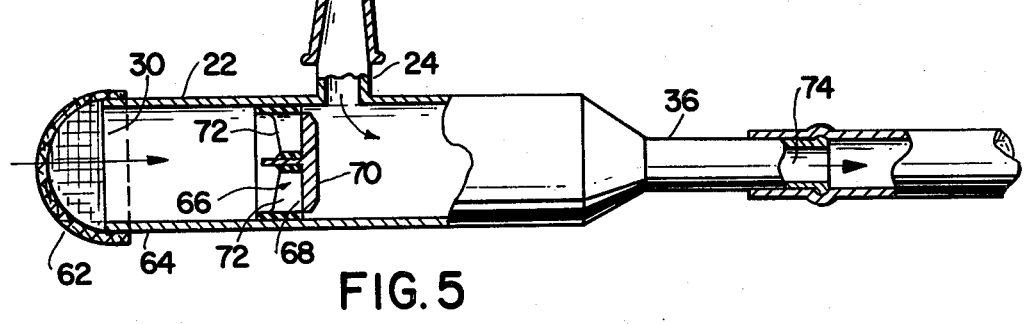
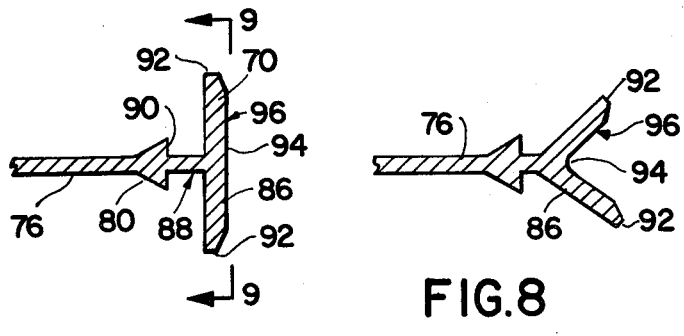
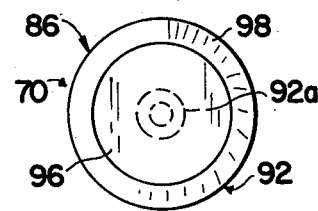

GAS SCAVENGER SYSTEM

This is a continuation-in-part application of Ser. No. 691,357 filed on 6/1/76 now abandoned.

BACKGROUND OF THE INVENTION

1. The Field of the Invention

This invention relates to anesthetic systems and more particularly to that class providing a closed exhaust discharge path for waste gases.

2. Description of the Prior Art

The prior art includes semi-closed and closed exhaust systems for disposing the waste gas products from anesthesia machines. U.S. Pat. No. 3,276,446 issued on Oct. 4, 1966 to W. W. Hay teaches a semi-closed anesthetic system utilizing a relief valve scheme for permitting the waste gases or administered gases, when exceeding a predetermined pressure level, to be vented to the atmosphere. The difficulty encountered with this invention is that operating room personnel, in proximity to the anesthesia machine, suffer pharmocological effects, such as discomfort or even cytotoxcity. Birth defects of the children of hospital personnel routinely exposed to waste gases admitted to the atmosphere is discussed by Corbett, T. H., Cornell, R. G., Endres, J. L., Leeding, K., "Birth Defects Among Children of Nurse Anesthetists." Anesthesiology 41: 341 -344, 1974. U.S. Pat. No. 3,604,488 issued on Sept. 14, 1971 to R. A. Marrese et. al. discloses a relief valve for an anesthetic gas line which can be utilized to conventionally discharge overloading anesthetic gas into the surrounding atmosphere, and which further is provided with a valve assembly for connection to a closed system so that the over-loading anesthetic gas is retained with the closed system and is not discharged to the surrounding atmosphere. Manual operaton of the valve selects between the two modes of waste gas removal. Both of the aforementioned patents suffer the common deficiency in which high levels of toxic gases may accumulate in the operating theater.

SUMMARY OF THE INVENTION

A primary object of the present invention is to provide a waste gas scavenger apparatus which discharges the waste gas accumulated thereby into a closed system, thus minimizing if not completely eliminating, discharge of the gas into the operating room.

Another object is to provide a waste gas accumulation bag which buffers the negative pressure from the vacuum line to the patient's breathing anesthetic circuit.

Still another object is to provide a scavenger valve, insensitive to moisture, which selectively decouples the discharge vacuum line from the accumulation bag when it is emptied.

Yet another object is to provide an air admitting port to the scavenger valve which when operated allows air to enter the vacuum line thus precluding the continual application of negative pressure, obtained from the vacuum line, to the patient's anesthetic circuit.

A further object is to provide a gas scavenger apparatus, inexpensive in constructional cost, which can be readily added to existing anesthesia machines.

A still further object is to provide a scavenger valve which is essentially failsafe and does not require metallic elements to bias the valve in a closed condition.

The ever increasing awareness of the pharmological effects of waste gas accumulations in the area surrounding anesthesia machines is beginning to become understood and a topic of concern to medical safety specialists. Closed circuit removal without optional discharge to the atmosphere, of waste gases, appears to represent the only practical solution to this problem. Such an apparatus must, however, permit existing anesthesia machines to operate substantially in the modes for which they have been designed whilst effectively performing the task of disposing of the waste gas.

These objects, as well as other objects of the present invention, will become more readily apparent after reading the following description of the accompanying drawings.

BRIEF DESCRIPTION OF THE DRAWINGS

FIG. 5 is a side-elevation view of another embodiment of the present invention.

FIG. 6 is a side elevation, expanded cross-sectional view of the valve mechanism illustrated in FIG. 5.

FIG. 7 is a side-elevational cross-sectional view, of the valve member illustrated in FIG. 6, when such valve is closed.

FIG. 8 is a side-elevational cross-sectional view of the valve member illustrated in FIG. 6 when the valve member is opened.

FIG. 9 is a front-elevational view taken in the direction of arrows 9—9, as shown in FIG. 7.

DESCRIPTION OF THE PREFERRED EMBODIMENT

Figure 1:
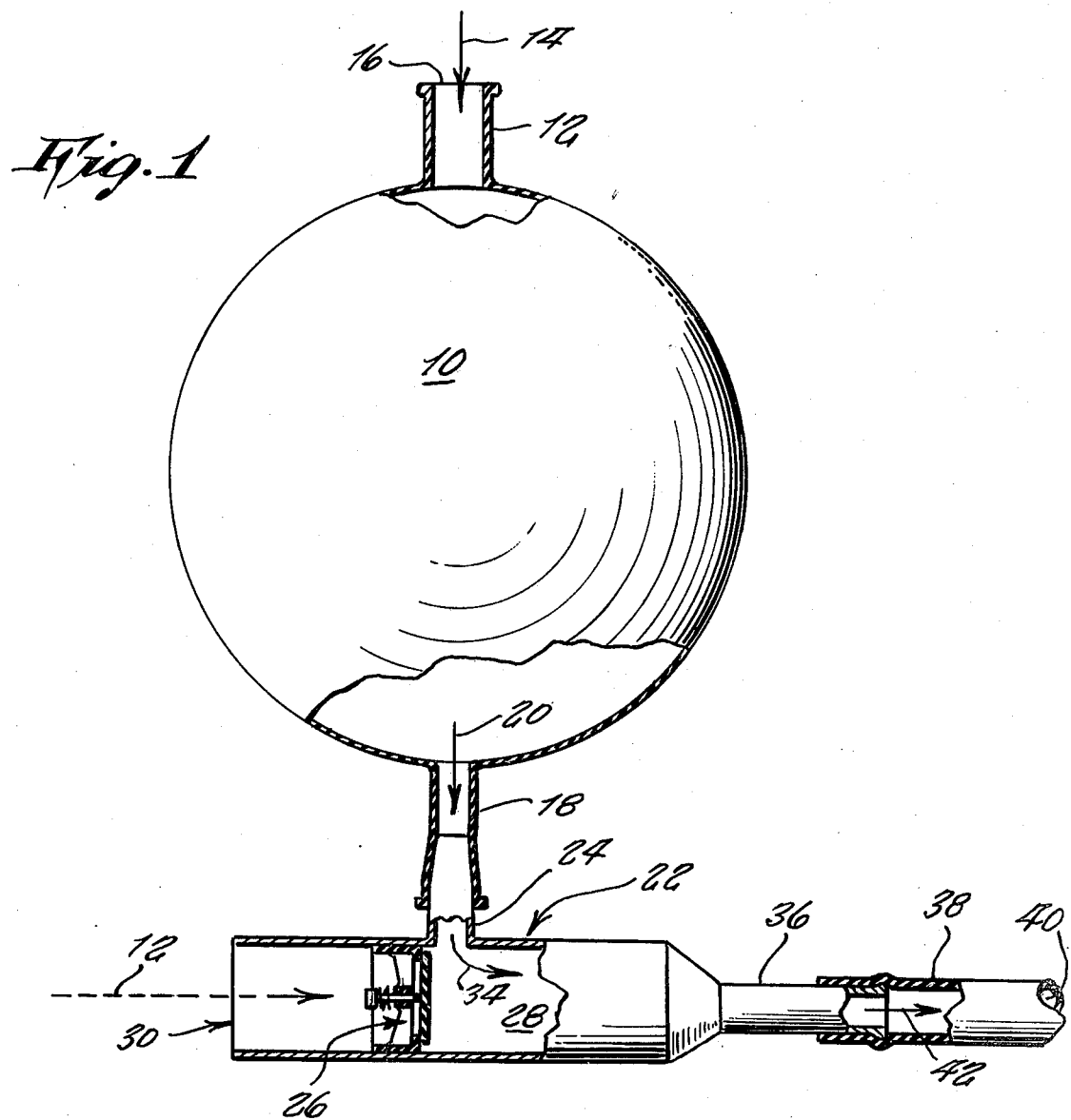
FIG. 1 is a side elevation partial cut-away view of the present invention.

The structure and method of fabrication of the present invention is applicable to a gas scavenger apparatus utilizing an accumulating bag which, when fully expanded, has a five liter capacity. A typical patient's anesthetic circuit is shown and described in U.S. Pat. No. 3,800,793, issued Apr. 2, 1974 to R. Marrese. Two ports are provided on the bag, one of which is connected to the patient's anesthetic circuit and passes waste gas from the patient's breathing bag to within the accumulating bag, the other port is connected to the body of a scavenger valve intermediate the location of a rubber air admitting check valve and a vacuum line. The check valve remains closed when the accumulating bag is partially or totally full, permitting the vacuum line to continually drain the accumulating bag. The check valve is closed preventing waste gas from seeping through the air admitting port into the atmosphere. When the accumulating bag is virtually empty, the vacuum line exerts an opening force on the check valve causing it to open thereby allowing atmospheric gas to be pulled into the scavenger valve and suctioned away by the vacuum line. When the scavenger valve is open, there is no negative pressure exerted on the accumulating bag thereby preventing any modification in the pressure levels within the anesthesia machine caused by the negative pressure from the vacuum line. When waste gas accumulates in the accumulating bag, the pressure differential experienced therewithin permits the scavenger valve to be closed, utilizing a biasing mechanism therefor, and allowing the accumulating bag to be slowly drained by the negative pressure supplied by the vacuum line.

The rubber air admitting check valve may be biased towards a valve seat utilizing a metallic spring therefor. An alternate embodiment utilizes a flat disc-like rubber valve member which is biased in a closed condition against the valve seat utilizing the resilient properties of the rubber-like member itself. When the accumulating bag is virtually empty, vacuum line causes the rubber-like valve member to distort so as to have the disc-like valve member fold such that the marginal edges thereof are disposed outwardly from the valve seat. Since no metallic spring biasing mechanisms are utilized therefor, the valve assembly, comprising the check valve, is virtually free from failures. Accumulated gases, injected into the gas scavenger apparatus from the atmosphere, are caused to pass through a screen-like filter disposed covering the air admitting port in the scavenger valve. Thus, dust or any other foreign particles, are not admitted into the scavenger valve. Furthermore, if the size of the outlet port of the scavenger valve is maintained approximately 80% of the size of the port communicating to the accumulating bag and when the outlet port of the scavenger valve is approximately 8 mm in diameter, that for a wide range of negative pressures and wide range of diameter of rubber-like valve elements that the negative pressure, in virtually any amount, being applied to the system, will not be transmitted to the patient's breathing bag. Finally, if the vacuum system that is applied to the outlet port, of the scavenger fails, the valve will close, thus preventing waste gases from entering the operating room through the inlet port of the scavenger valve. However, the waste gases will still be forced out through the outlet port of the scavenger valve, and along the vacuum line without causing excessive positive pressure in the patient's breathing circuit.

Now referring to the Figures, and more particularly to the embodiment illustrated in FIG. 1 showing an accumulating bag 10 having an inlet tube 12 which provides waste gas in the direction of arrow 14 into orifice 16. Outlet tube 18 allows the accumulated gas not shown, to leave the accumulating bag 10 in the direction of arrow 20. Scavenger valve housing 22 is provided with inlet tube 24, pneumatically connected to outlet tube 18. Valve 26, shown in the closed position, prevents operating room air, not shown, from entering cavity 28 by way of opening 30. When valve 26 is opened, operating air will enter opening 30, in the direction of arrow 32, and traverse into cavity 28 mixing with the waste gas, not shown, entering cavity 28 from tubes 18 and 24, in the direction of arrow 34. Cavity 28 terminates in pipe 36 which is pneumatically connected to tubing 38. End 40 of tubing 38 is connected to a vacuum line, not shown, causing the flow of gas or air in the direction of arrow 42.

Figures 2, 3, 4:
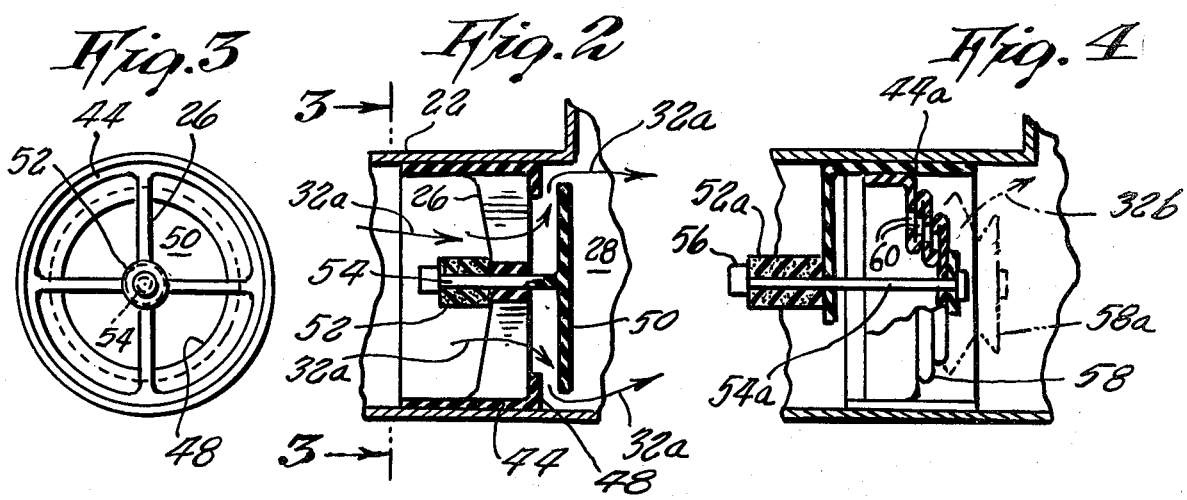
FIG. 2 is an expanded cross-sectional side elevation view of the valve mechanism illustrated in FIG. 1.
FIG. 3 is a side-elevational cross-sectional view taken along line 3—3 viewed in the direction of arrows 3—3 as shown in FIG. 2 illustrating the valve seat and spider assembly of the valve.
FIG. 4 is a side elevational cross-sectional view of an alternate embodiment of a valve apparatus.

FIG. 2 illustrates the valve mechanism 26, shown in FIG. 1, having a hard rubber tubular section 44 to which is suspended spider 46. Shoulders 48 enable port closing member 50 to close off the flow of air from the atmosphere to void 28 when seated thereupon. Sponge rubber cylinder 52 tends to bias port closing member 50 in the closed position thus preventing the flow of air in the direction of arrows 32a. The choice of rubber for this vital valve function precludes misoperation due to sticking upon the accumulation of moisture.

FIG. 3 illustrates rubber tubular section 44 and shoulders 48 against which port closing member 50 seats. Spider 26 supports sponge rubber cylinder 52 through which shaft 54 passes.

FIG. 4 employs a hard rubber tubular section 44a to which is afitted a sponge rubber biasing member 52a. Rod 54a is capped at one end by caps 56 and engages a flexible resilient rubber-like convoluted perforated valve member 58. Openings 60 are closed when valve member 58 is in the convoluted position shown and opened when in the position designated by dotted lines and numerals 58a, allowing air to pass in the direction of arrow 32b.

FIG. 5 is another embodiment of the present invention showing the accumulating bag 10 coupled to scavenger valve housing 22, in similar fashion to that shown in FIG. 1. Wire-like screen 62 is disposed covering inlet port 30 and is provided having a conical shape. Screen 62 may be press fit over exterior surface 64 of housing 22. Valve seating member 66 is shown having a flat surface 68 engaging port closing member 70. Such port closing member is provided having a flat surface opposing flat surface 68 and closing off openings disposed intermediate radial fin-like arms 72. The diameter of communicating port diameter inlet tube 24 adjacent surface 64 is shown equal in size to the internal diameter at point 74 of pipe 36. As seen, port closing member 70 is shown closing off the flow of air from the atmosphere communicating to point 74, after passing through screen 72.

FIG. 6 illustrates port closing member 70, in the closed position against the openings formed by radially disposed arms 72. Stem 76, of port closing member 70 is affixed to flat surface 78 thereof and extends outwardly therefrom. Conically shaped protrusion 80 extends outwardly from the surface of rubber-like element 76 so as to capture port closing member 70 against escape from opening 82. As shown, air flowing in the direction of arrow 84 will not go beyond port closing member 70 due to the rubber-like resilient characteristics of cap portion 86 of rubber-like member 70.

FIG. 7 illustrates port closing member 70 having protrusion 80 extending radially outwardly from rod-like portion 76. Region 88 is shown having a diameter suitable for retention in opening 82, shown in FIG. 6. Flat side 90, of protrusion 80, is disposed resting against radially disposed arms 72, adjacent opening 82, shown in FIG. 6. In the position shown, cap portion 86 resides transverse to rod-like portion 76, due to the resiliant memory of rubber-like port closing member 70. Marginal edges 92, of cap member 86, are disposed defining a plane passing through point 94, shown centered in surface 96, of cap portion 86.

FIG. 8 illustrates port closing member 70 wherein cap portion 86 is shown distorted due to the flow of air, in the direction of arrow 84 shown in FIG. 6, so as to cause marginal edges 92 to move outwardly from point 94 in surface 96. In this position, port closing member 70 permits air to move in the direction of arrow 84 shown in FIG. 6 and to enter the confines of pipe 36, shown in FIG. 5.

FIG. 9 illustrates surface 96 of cap member 86. Region 98 of surface 96, adjacent marginal edge 92 thereof, is tapered downwardly towards flat surface 90 shown in FIG. 7, depicted herein by dotted lines 92a. Such tapering facilitates the folding of marginal edges 92 thereby making port closing member 70 more pliable and more reliable.

One of the advantages is to provide a waste gas scavenger apparatus which discharges the waste gas accumulated thereby into a closed system, thus minimizing if not completely eliminating, discharge of the gas into the operating room.

Another advantage is to provide a waste gas accumulation bag which buffers the negative pressure from the vacuum line to the patient's breathing anesthetic circuit.

Still another advantage is to provide a scavenger valve, insensitive to moisture, which selectively decouples the discharge vacuum line from the accumulation bag when it is emptied.

Yet another advantage is to provide an air admitting port to the scavenger valve which when operated allows air to enter the vacuum line thus precluding the continual application of negative pressure, obtained from the vacuum line, to the patient's anesthetic circuit.

A further object is to provide a gas scavenger apparatus, inexpensive in constructional cost, which can be readily added to existing anesthesia machines.

Thus, there is disclosed in the above description and in the drawings, an embodiment of the invention which fully and effectively accomplishes the objects thereof. However, it will become apparent to those skilled in the art, how to make variations and modifications to the instant invention. Therefore, this invention is to be limited, not by the specific disclosure herein, but only by the appending claims.

The embodiment of the invention in which an exclusive privilege or property is claimed are defined as follows:

1. A gas scavenger apparatus comprising an accumulating bag, said accululating bag having a pair of openings therein, one of said pair of openings for coupling to a patient's anesthetic circuit, accumulator bag emptying means defining a passageway having first and second inlet parts and an outlet part, said second inlet part located intermediate said first inlet part and said outlet part, vacuum means connected to said outlet part, valve means coupled intermediate said first inlet part and said second inlet part for selectively admitting surrounding air into said passageway, said other of said pair of openings of said accumulating bag for selectively emptying said accumulating bag being connected to said second inlet part of waste gas accumulated therein when said valve means are closed and to discharge said waste gas simultaneously into said vacuum means, bias means for urging said valve means in said closed position when said waste gas is being emptied, said accumulating bag emptying means admitting said surrounding air and simultaneously emptying said accumulating bag when said valve means is in an open position, means to filter said surrounding air passing through said first inlet part when said valve means is in said open position, said valve means including a disc shaped rubber-like member and a flat valve seat, said valve seat having an opening therein, said disc shaped rubber-like member being disposed closing said opening in said flat valve seat when said valve means is in said closed position, the marginal edges of said disc being disposed outwardly from said valve seat when said valve means is in said open position.

2. The gas scavenger apparatus as claimed in claim 1 wherein said accumulator bag emptying means includes a housing having said passageway extending therethrough, said first inlet part located at one end of said housing and communicating with said passageway, said outlet part located at the other end of said housing and communicating with said passageway, and said second inlet part located intermediate said first inlet part and said outlet part in said housing and communicating with said passageway, said passageway, between said second inlet part and said outlet part, defining a mixing cavity, said valve means opened upon the presence of sufficient negative pressure in said mixing cavity, said vacuum means including a vacuum line connected to said outlet part.

3. The gas scavenger apparatus as claimed in claim 2 wherein said valve means comprises said flat valve seat being located intermediate said first inlet port and said mixing cavity, the outermost marginal edges of said valve seat secured to the innermost surfaces of said passageway in said housing, a plurality of radial arms extending radially outwardly from the center of said opening, a hole disposed at the juncture of said plurality of said radial arms located at said center of said opening, a T shaped opening sealing member comprising said disc possessing rubber-like qualities and a rod affixed normally to said disc, said rod possessing rubber-like qualities and passing through said hole, said bias means causing said disc to be disposed in touching engagement with flat valve seat adjacent said opening therein by exerting a biasing force on said disc directing said marginal edges of said disc towards said flat valve seat.

4. The gas scavenger apparatus as claimed in claim 3 further comprising said rod having a protrusion extending radially outwardly therefrom for securing said rod in said hole and thereby holding said disc against said valve seat.

5. The gas scavenger apparatus as claimed in claim 1 wherein said accumulating bag has an inflated capacity of five liters.

6. The gas scavenger apparatus as claimed in claim 1 wherein said accumulating bag emptying means comprises said valve means being disposed in said closed position and said accumulating bag emptying solely into said vacuum means.

7. The gas scavenger apparatus as claimed in claim 1 wherein said bias means comprises said disc urging said said marginal edges towards said opening in said flat valve seat.

* * * * *